US010657372B2

(12) United States Patent
Pattnaik et al.

(10) Patent No.: US 10,657,372 B2
(45) Date of Patent: May 19, 2020

(54) SYSTEMS AND METHODS FOR IDENTIFYING AND DISPLAYING OPTIMAL LOCATIONS FOR A GARDEN (71) Applicant: Walmart Apollo, LLC, Bentonville, AR (US)

(72) Inventors: Suman Pattnaik, Bentonville, AR (US); Matthew Dwain Biermann, Fayetteville, AR (US); Steven Jackson Lewis, Bentonville, AR (US)

(73) Assignee: Walmart Apollo, LLC, Bentonville, AR (US)

( * ) Notice: Subject to any disclaimer, the term of this patent is extended or adjusted under 35 U.S.C. 154(b) by 290 days.

(21) Appl. No.: 15/882,979

(22) Filed: Jan. 29, 2018

(65) Prior Publication Data
US 2018/0232578 A1 Aug. 16, 2018

Related U.S. Application Data (60) Provisional application No. 62/459,677, filed on Feb. 16, 2017.

(51) Int. Cl.
*G06K 9/00* (2006.01)
*G01N 33/24* (2006.01)
(Continued)

(52) U.S. Cl.
CPC ....... *G06K 9/00657* (2013.01); *A01D 34/008* (2013.01); *A01G 7/00* (2013.01);
(Continued)

(58) Field of Classification Search
USPC .................................................. 382/100, 103
See application file for complete search history.

(56) References Cited

U.S. PATENT DOCUMENTS 9,924,629 B2 * 3/2018 Batcheller ............ A01C 21/005
10,338,272 B2 * 7/2019 Xiang .................... G01N 21/17
(Continued)

OTHER PUBLICATIONS

Edyn, Keep tabs on your garden with the Edyn Garden Synsor. Retrieved online at: https://edyn.com/. 11 pages. Retrieved Nov. 30, 2016.
(Continued)

*Primary Examiner* — Ishrat I Sherali
(74) *Attorney, Agent, or Firm* — McCarter & English, LLP; David R. Burns (57) ABSTRACT A system for identifying and displaying one or more optimal locations within a lot for a garden in which to plant and grow suggested plant varieties is discussed. The system includes a robotic device positioned and configured to scan the lot and to generate at least one lot parameter. The system also includes a soil sensor positionable in soil in the lot and configured to generate at least one soil parameter. The system further includes a computing system configured to execute a location optimization module that determines varieties of suggested plants based on the soil parameter and the lot parameter. Based on a user selection from the varieties of suggested plants, the computing system identifies optimal locations for a garden within the lot for the one or more selected plants. The computing system transmits the optimal locations for the garden to a user computing device for display.

20 Claims, 4 Drawing Sheets (51) Int. Cl.
*A01G 7/00* (2006.01)
*A01G 22/00* (2018.01)
*A01D 34/00* (2006.01)
*A01G 25/16* (2006.01)
*G06T 11/60* (2006.01)
*G05D 1/00* (2006.01)
*G05D 1/02* (2020.01)
*G05D 1/10* (2006.01)

(52) U.S. Cl.
CPC ........... *A01G 22/00* (2018.02); *A01G 25/167* (2013.01); *G01N 33/24* (2013.01); *G06K 9/00671* (2013.01); *G01N 33/246* (2013.01); *G01N 2033/245* (2013.01); *G05D 1/0088* (2013.01); *G05D 1/021* (2013.01); *G05D 1/10* (2013.01); *G06T 11/60* (2013.01)

(56) References Cited

U.S. PATENT DOCUMENTS

| | | | |
|---|---|---|---|
| 10,342,174 B2 * | 7/2019 | Xu | A01B 79/005 |
| 10,491,655 B2 * | 11/2019 | Borlik | G06Q 20/145 |
| 2002/0059186 A1 | 5/2002 | Weber et al. | |
| 2009/0216661 A1 | 8/2009 | Warner | |
| 2011/0054921 A1 | 3/2011 | Lynds | |
| 2015/0164009 A1 | 6/2015 | Chandran et al. | |
| 2019/0116719 A1 * | 4/2019 | Fletcher | A01B 79/005 |
| 2019/0139158 A1 * | 5/2019 | Reich | G06N 3/006 |
| 2019/0289786 A1 * | 9/2019 | Prystupa | A01B 79/005 |

OTHER PUBLICATIONS

GreenIQ, GreenIP Smart Garden Hub, The System Technology, Controls Irrigation, Saves Water. Retrieved online at: http://greeniq.co/product_tech.htm. 3 pages. (2016).

Helmer, How a Green Thumb Is Helping This Entrepreneur Earn Greenbacks. Retrieved online at: https://www.entrepreneur.com/article/242509. 5 pages. Mar. 9, 2015.

Sathiesh et al., Smart Autonomous Gardening Rover with Plant Recognition using Neural Networks. Procedia Computer Science. 2016;93:975-981.

* cited by examiner

FIG. 4

SYSTEMS AND METHODS FOR IDENTIFYING AND DISPLAYING OPTIMAL LOCATIONS FOR A GARDEN

CROSS-REFERENCE TO RELATED PATENT APPLICATIONS

This application claims priority to U.S. Provisional Application No. 62/459,677 filed on Feb. 16, 2017, the content of which is hereby incorporated by reference in its entirety.

BACKGROUND

There are a number of factors, such as geography and soil composition, which dictate how well certain types and varieties of plants may grow in a garden. Other factors such as shade and elevation at the location of the garden may also impact plant growth. Additionally, the time of year may also contribute to the success or failure of a planting within the garden.

BRIEF DESCRIPTION OF THE DRAWINGS

The accompanying drawings, which are incorporated in and constitute a part of this specification, illustrate one or more embodiments of the invention and, together with the description, help to explain the invention. The embodiments are illustrated by way of example and should not be construed to limit the present disclosure. In the drawings.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION OF THE DISCLOSURE

Systems and methods are described herein for a system for identifying and displaying one or more optimal locations within a lot for a garden in which to plant and grow suggested plant varieties. In one embodiment, the system includes at least one robotic device, such as a rover or unmanned aerial vehicle (i.e. a drone), positioned and configured to scan the lot and generate at least one lot parameter. The system also includes at least one soil sensor positionable in soil in the lot and configured to generate at least one soil parameter. The system includes a storage device storing predefined criteria for associating plant varieties, lot parameters, and soil parameters with optimal lot locations. The system further includes a computing system communicatively coupled to the robotic device, the soil sensor, the storage device, and a user computing device. The user computing device is configured to display one or more optimal locations within the lot for the garden.

In one embodiment, the computing system is configured to execute a location optimization module that when executed receives at least one lot parameter from at least one robotic device and at least one soil parameter from at least one soil sensor. The location optimization module determines one or more varieties of suggested plants based on the soil parameter and the lot parameter. For example, the location optimization module may consult a database containing acceptable soil parameter-lot parameter combinations for different plant varieties. Soil parameters determined by the soil sensor may be, but are not limited to, a moisture content level of the soil, a potential hydrogen (pH) level of the soil, a temperature level of the soil, and an intensity level of light that reaches the soil. Lot parameters identified by the robotic device may be, but are not limited to, a lot area size, a geographic location, a date, an identification of water sources, an elevation, an identification of buildings located in the lot, a current garden layout, an identification of trees and shrubbery, and shade density information for locations within the lot. The location optimization module transmits an identification of the one or more varieties of suggested plants to the user computing device. The user computing device displays the identification of the one or more varieties of suggested plants to a user. The location optimization module receives, from the user computing device, a selection of one or more plants from the group of suggested plants. Following the receipt of the selection of the suggested plants, the location optimization module generates one or more optimal locations of a garden in the lot for the selected plants based on the lot parameter(s), the soil parameter(s), and the predefined criteria. For example, the location optimization module may consult a database containing optimal location criteria for the selected plant or plants. In one embodiment, the criteria may have been previously accumulated from past feedback from gardeners or others indicating positive results from locating the selected plants in a particular manner. For example, the criteria may indicate that selected plant A should be located in a shady portion of the lot while plant B should be located in a sunny portion of the lot. Similarly, the criteria may indicate that plant C needs to be located a certain distance away from any other plants when laying out the garden within the lot. The one or more optimal locations represent a portion of the lot that is less than the entire lot. The location optimization module transmits the one or more optimal locations of the garden to the user computing device. In one embodiment, the user computing device displays the one or more optimal locations of the garden in the lot on a map (i.e., a topographical map, an atlas map, or a street map).

In additional embodiments, the system further includes a specialized application that assists in locating a garden that is installed on the user computing device. The user computing device includes a camera configured to capture one or more images of the lot. The application is configured to use augmented reality to display the optimal location of the garden received from the location optimization module within a depiction of the lot created using the one or more images. In further embodiments, the application is further configured to use augmented reality to display an arrangement of the one or more varieties of suggested plants in the garden. In additional embodiments, the application is further configured to use augmented reality to display the one or more varieties of suggested plants in full bloom in the garden.

Plants as described herein include any variety of plant crops including, but limited to, flowers, vegetables, fruits, bushes, and trees.

Figure 1:
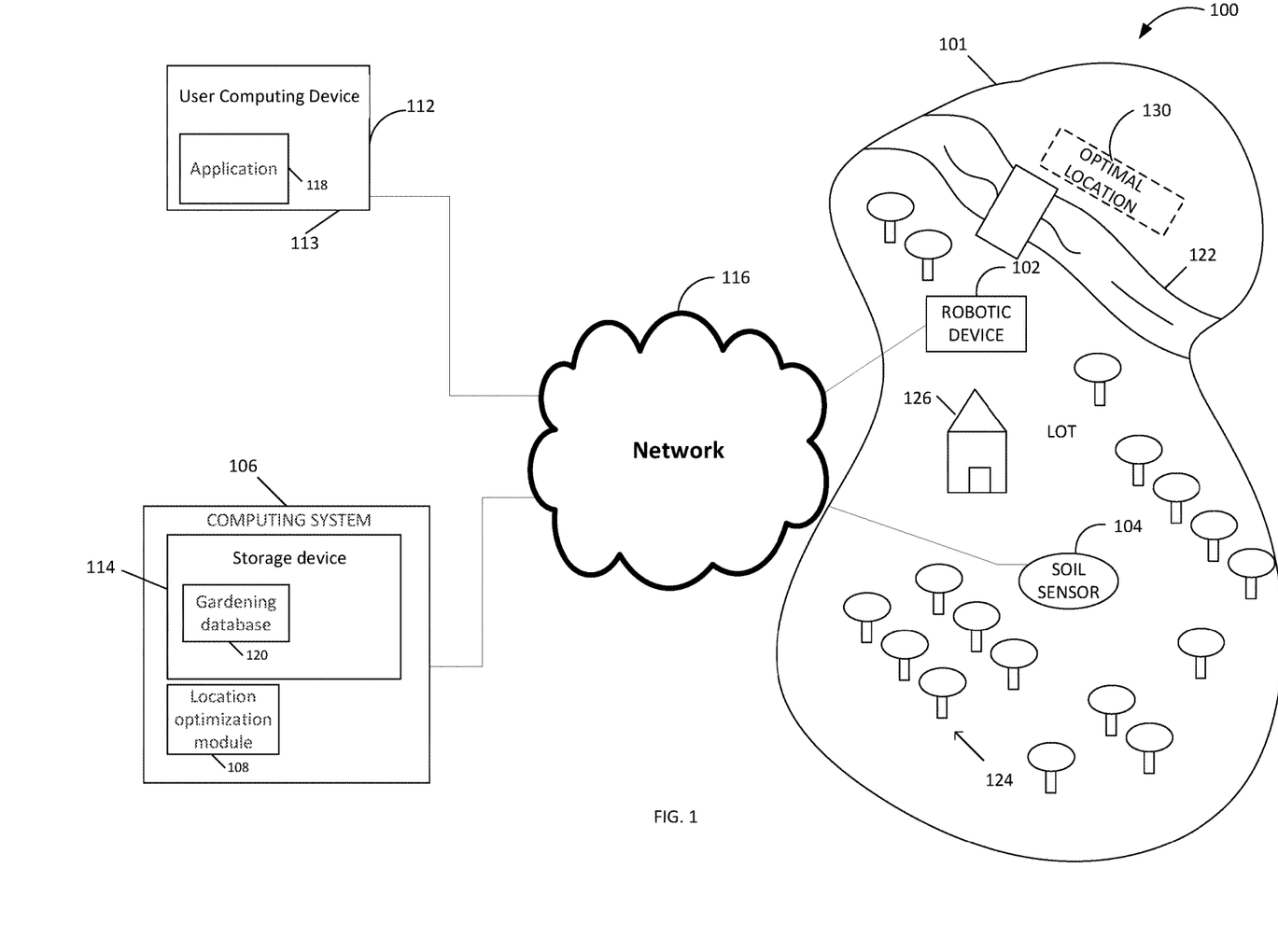
FIG. 1 is a block diagram of an exemplary system for identifying and displaying one or more optimal locations within a lot for a garden in which to plant and grow suggested plant varieties, according to an example embodiment.

FIG. 1 is a block diagram of an exemplary system 100 for identifying and displaying one or more optimal locations of a garden in a lot 101 to plant and grow suggested plant varieties, according to an embodiment. System 100 includes at least one robotic device 102, at least one soil sensor 104, at least one user computing device 112, and a computing system 106. The computing system 106 includes at least one location optimization module 108. The user computing device 112 (e.g. a user smartphone) includes at least one application 118. The computing system 106 and user computing device 112 are communicatively coupled to a storage device 114 over a network 116. Storage device 114 includes one or more databases for storing data and information related to location optimization module 108, application 118, and any use thereof. Computing system 106 may include one or more server computers to execute modules (e.g., location optimization module 108), service user connections, and/or manage databases in computing system 106.

In an embodiment, location optimization module 108 includes logic, functions, rules, or operations to provide varieties and forms of user interfaces for a user to interact with system 106 via application 118 executing on user computing device 112. Location optimization module 108 is configured to interact with application 118. In some embodiments, application 118 includes a graphical user interface having user interface elements arranged and combined in a suitable manner and displayed on a display 113 to receive input from a user and/or display output, data and information to the user. In an exemplary embodiment, application 118 is configured to provide the graphical user interface for a user to at least (i) view an identification of one or more varieties of suggested plants, (ii) select one or more plants of the one or more varieties of suggested plants, and (iii) view one or more optimal locations of a garden in lot 101, as described herein.

Storage device 114 includes a gardening database 120 that includes a database of gardening knowledge. In one embodiment, gardening database 120 includes detailed information for varieties of plants for a garden. For example, gardening database 120 may include data providing a plant's specific properties, growing characteristics, yield, soil requirements, environmental requirements, maintenance and installation requirements, nutritional content and other related information. The system supports garden elements that are grown or plantable as well as non-plantable elements that may support or inhibit a garden. As such, gardening database 120 provides information to assist location optimization module 108 in selecting a location of a garden in lot 101 based on the suggested plants selected by the user.

In some embodiments, storage device 114 stores, tracks and manages data and information of one or more garden locations. For example, storage device 114 may store information on a location of the garden in lot 101. Storage device 114 may also store user plant selections.

In system 100, at least one robotic device 102 is positioned in lot 101. In an exemplary embodiment, robotic device 102 is configured to scan lot 101 and generate at least one lot parameter. In one embodiment, robotic device 102 is an autonomous land rover configured to circulate within lot 101 during scanning. In another embodiment, robotic device 102 is an unmanned aerial vehicle (i.e., a drone) configured to fly over lot 101 while scanning. In one embodiment, robotic device 102 is communicatively coupled to network resources and may also include a GPS receiver. In a further embodiment, robotic device 102 may be one or more stationary scanners positioned within or proximate to lot 101 and configured to scan lot 101. The lot parameter identified by the robotic device 102 may include, but is not limited to, at least one of a lot area size, a geographic location, a date, a season, climate conditions, an identification of water sources, an elevation, an identification of buildings located in the lot, a current garden layout, an identification of trees and shrubbery, and a determination of shade density. For example, robotic device 102 may be configured to identify a stream 122, trees 124, and a structure 126 in lot 101. Robotic device 102 may further be configured to identify and assign sunlight patterns to locations throughout lot 101. In an exemplary embodiment, the sunlight patterns are full sun, partially shaded, or completely shaded.

System 100 further includes at least one soil sensor 104 positionable in soil in lot 101 and configured to generate at least one soil parameter. As noted above, the at least one soil parameter may include, but is not limited to at least one of a moisture content level of the soil, a potential hydrogen (pH) level of the soil, a temperature level of the soil, and an intensity level of light that reaches the soil. In one embodiment, the at least one soil sensor 104 is attached to the autonomous rover or may be deployed from a drone.

The at least one soil parameter and the at least one lot parameter are transmitted to location optimization module 108 via network 116. In one embodiment, location optimization module 108 may determine one or more varieties of suggested plants based on the at least one soil parameter and the at least one lot parameter. In another embodiment, location optimization module 108 may determine one or more varieties of suggested plants based on the at least one lot parameter without relying on a soil parameter. Location optimization module 108 may be configured to determine plantable elements in lot 101 based on layout, size, soil conditions, climate or weather conditions, geographic location, yield, costs, aesthetics, nutritional value, intra-garden plant compatibility, ease or difficulty of installation and/or maintenance, etc.

In one non-limiting example, location optimization module 108 determines one or more varieties of suggested plants suitable for lot 101 depending on the plant varieties that can tolerate the environmental conditions in lot 101. The environmental conditions are based on, for example, the at least one soil parameter and the at least one lot parameter. For example, a rating may be generated for each plant variety. The rating specifies a degree of suitability of the plant variety with respect to lot 101, such as elevation, soil quality, and environmental conditions at lot 101. Location optimization module 108 suggests a plant if the rating is above a predefined threshold. As will be understood by one of ordinary skill in the art, a number of levels of ratings may be used. Plant varieties that can tolerate the conditions of lot 101 are determined to be suitable and are included as plants selectable by the user for inclusion in a garden in lot 101. Plant varieties that cannot tolerate the conditions of lot 101 are determined to be unsuitable. Unsuitable plant varieties are marked and excluded as options selectable by the user for inclusion in a garden in lot 101.

Location optimization module 108 transmits an identification of the one or more varieties of suggested plants to user computing device 112 for the user to choose from. Application 118 on user computing device 112 displays the identification of the one or more varieties of suggested plants. For example, the user may be presented with a list or a set of thumbnail images representing the variety of suggested plants. User computing device 112 may include an input device, such as a touch screen or mouse, to enable the user to select one or more plants from the one or more varieties of suggested plants for the garden. After a user selection of one or more plants to include in the garden a list of the plants selected by the user may be stored in storage device 114.

Location optimization module 108 receives, from user computing device 112, the selection of the one or more plants of the one or more varieties of suggested plants. The selection defines which plants will be planted in the garden and is used to design the location of the garden. In some embodiments, location optimization module 108 receives dimensions of the lot from user computing device 112, and determines the one or more optimal locations of the garden within the dimensions of the lot.

Location optimization module 108 generates one or more optimal locations of a garden in lot 101 for the one or more selected plants based on the at least one soil parameter, the at least one lot parameter, and the predefined criteria. In an exemplary embodiment, each optimal location includes a size, a shape, and an orientation of the garden in the optimal location. The predefined criteria includes predefined factors that associate a plant variety with an optimal location. The predefined factors may include environmental conditions required by each plant variety. Location optimization module 108 determines whether the one or more selected plants are suitable for locations throughout lot 101 by determining whether the requirement of the one or more selected plants are met by the environmental conditions in each location. The environmental conditions are based on the at least one soil parameter providing an indication of soil quality and the at least one lot parameter providing an indication of a number of types of other lot characteristics as discussed above. A rating may be generated for each selected plant in each locations in lot 101. The rating specifies a degree of suitability of the plant with respect to the location, such as soil quality and environmental conditions at the location. In another non-limiting embodiment, the rating specifies a plant to be "good", "fair" or "poor" fit for each location. Location optimization module 108 may determine a location is optimal for a plant if the rating is above a predefined threshold. Plants that cannot tolerate the environmental conditions are determined to be unsuitable for the location. As will be understood by one of ordinary skill in the art, any number of levels of ratings may be used.

In a non-limiting example, as each plant may be associated with particular sunlight requirements and location optimization module 108 uses the lot parameters, in particular sunlight patterns determined in different locations of lot 101, to compare the sunlight patterns with sunlight requirements for each selected plant. For example, if the sunlight requirements for a plant is full sun and a location in lot 101 is associated with full sun, then the location is determined to be potentially suitable for a planting of the plant. If the sunlight requirement is partial shade and a location in lot 101 is associated with partial shade, then the location is determined to be potentially suitable. If the sunlight requirement is shade and a location in lot 101 is full shade, then the location is determined to be potentially suitable. Conversely, if the sunlight requirement is shade and a location in lot 101 is full sun, then the location is determined to be unsuitable.

After determining the sunlight requirements, location optimization module 108 may further determine whether a potentially suitable location determined above is also suitable based on, for example, the water requirements for each plant. For example, if the water requirements for a plant is a location near a water source, and the potentially suitable location is near stream 122, then the location remains suitable for an optimal garden location. Conversely, if the potentially suitable location is not near a water source, the location is determined to be unsuitable. Location optimization module 108 may repeat this procedure for a predefined number of plant requirements (i.e., temperature, elevation, soil quality, etc.) before determining one or more optimal locations that meet the requirements of the one or more selected plants. In one embodiment, the plant requirements considered by location optimization module 108 may be configurable based on input provided via a user interface generated by application 118 on user computing device 112.

In the non-limiting example, if, for example, the sunlight conditions and the water conditions of a location are suitable for the one or more selected plants, location optimization module 108 may determine that the location is an optimal location for a garden to plant and grow the one or more selected plants. In the non-limiting example, location optimization module 108 may determine that location 130 is an optimal location of a garden for one or more selected plants that require full sun and a location near a water source.

Location optimization module 108 transmits the one or more optimal locations of the garden to application 118 on user computing device 112. Application 118 displays the one or more optimal locations of the garden in lot 101, for example, on a map using a GPS location of the garden. The one or more optimal locations may specify the location and a length, a width, and an orientation of the garden bed at the location. A visual representation of the garden bed may be drawn to scale (where the length and width of the representation of the garden bed are presented in proportion to the length and width determined by location optimization module 108). In some embodiments, application 118 is configured to capture one or more images of lot 101 using a camera installed in user computing device 112. Application 118 may be configured to use augmented reality to display the one or more optimal locations of the garden within a depiction of lot 101 created using the one or more images. Application 118 may further be configured to use augmented reality to display an arrangement of the selected plants in the garden. In some embodiments, the augmented reality displays the selected plants in the garden at full bloom. For example, in some embodiments, application 118 is installed on an AR-enabled mobile device equipped with a Qualcomm® Snapdragon™ processor, where the components of processor are equipped to simultaneously process data from multiple sensors (gyroscope, accelerometer, and camera sensors).

Figure 2:
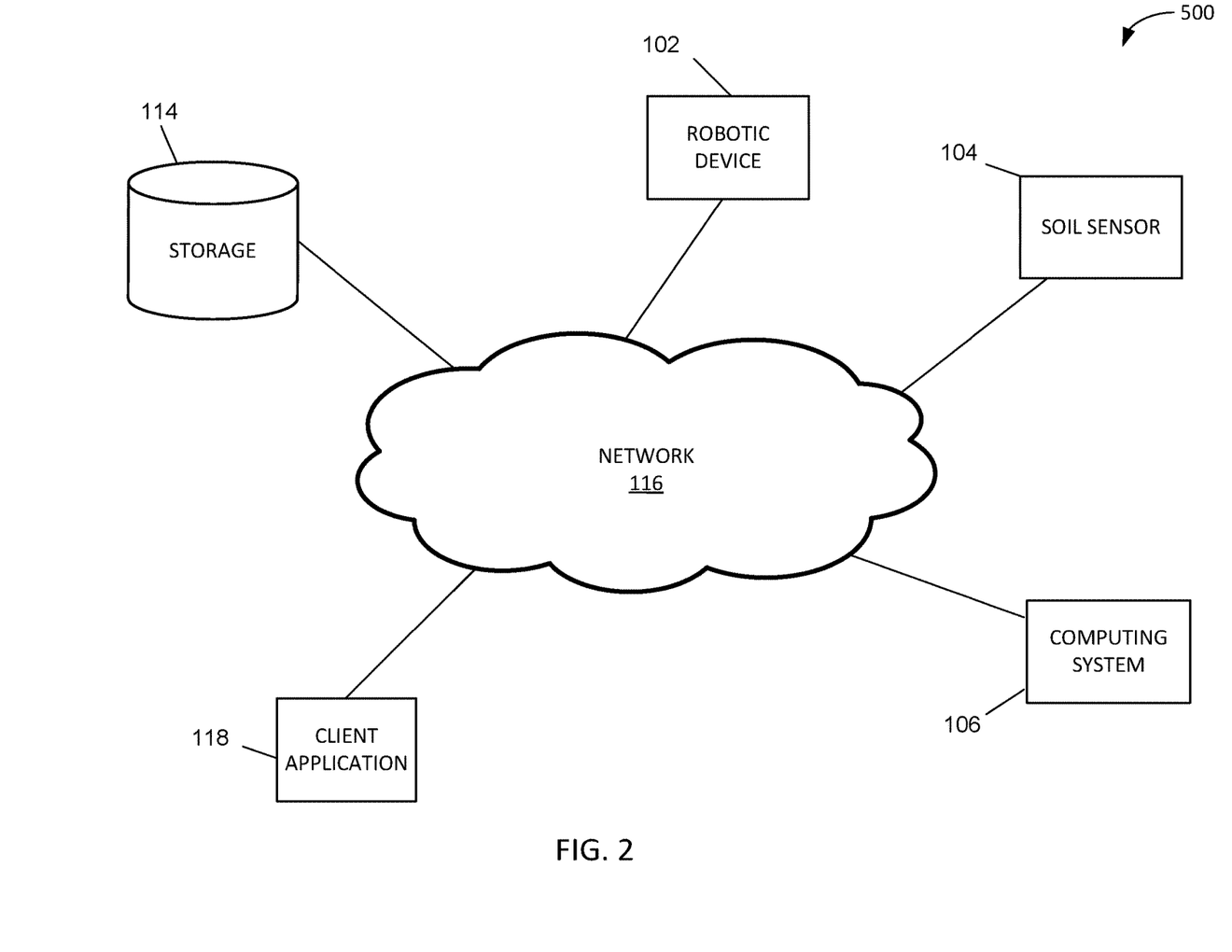
FIG. 2 illustrates an exemplary network suitable for use in an embodiment.

FIG. 2 illustrates a network diagram depicting a system 200 for identifying and displaying one or more optimal locations of a garden in a lot to plant and grow suggested plant varieties, according to an example embodiment. System 200 includes a network 116, at least one user device including application 118, at least one computing system 106, at least one robotic device 102, at least one soil sensor 104, and at least one storage device 114. Application 118, computing system 106, storage device 114, the at least one robotic device 102, and the at least one soil sensor 104 are in communication with network 116.

In an example embodiment, one or more portions of network 116 may be an ad hoc network, an intranet, an extranet, a virtual private network (VPN), a local area network (LAN), a wireless LAN (WLAN), a wide area network (WAN), a wireless wide area network (WWAN), a metropolitan area network (MAN), a portion of the Internet, a portion of the Public Switched Telephone Network (PSTN), a cellular telephone network, a wireless network, a WiFi network, a WiMax network, any other variety of network, or a combination of two or more such networks. In one embodiment, the specialized computer file system may be implemented for a corporation using its intranet or an internal network.

Application 118 may be associated with or installed on, but is not limited to, work stations, computers, general purpose computers, Internet appliances, hand-held devices, wireless devices, portable devices, wearable computers, cellular or mobile phones, portable digital assistants (PDAs), smart phones, tablets, ultrabooks, netbooks, laptops, desktops, multi-processor systems, microprocessor-based or programmable consumer electronics, network PCs, mini-computers, and the like. Application 118 may connect to network 116 via a wired or wireless connection. Application 118 may include one or more applications such as, but not limited to, a web application (e.g., browser 215 of computing device 300 shown in FIG. 3) and/or a mobile application to enable access to computing system 106 described herein.

Figure 3:
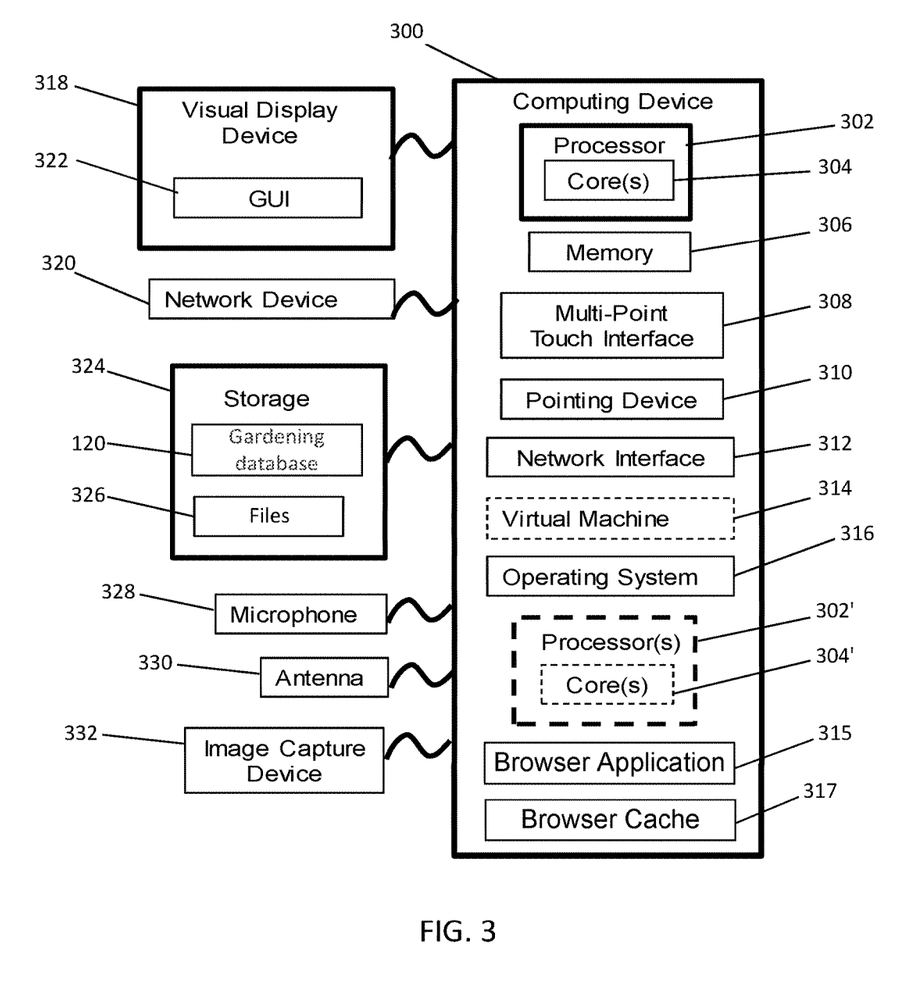
FIG. 3 is a block diagram of an exemplary computing device suitable for use in an embodiment.

Storage device 114 and computing system 106 are connected to network 116 via a wired connection. Alternatively, storage device 114 and computing system 106 may be connected to network 116 via a wireless connection. Computing system 106 comprise one or more computers or processors configured to communicate with application 118 via network 116. Computing system 106 can include one or more components of computing device 300 of FIG. 3A.

Storage device(s) 114 may include one or more storage devices for storing files and/or data retrievable by computing system 106. Storage device(s) 114 and computing system 106 may be located at one or more geographically distributed locations from each other or from application 118. Alternatively, storage device(s) 114 may be included within computing system 106.

FIG. 3 is a block diagram of an exemplary computing device 300 that can be used to perform one or more steps of the methods provided by exemplary embodiments. In an exemplary embodiment, computing device 300 is a computing system (i.e., computing system 106) and/or a user device (i.e., user computing device 112). Computing device 300 includes one or more non-transitory computer-readable media for storing one or more computer-executable instructions or software for implementing exemplary embodiments. The non-transitory computer-readable media can include, but are not limited to, one or more varieties of hardware memory, non-transitory tangible media (for example, one or more magnetic storage disks, one or more optical disks, one or more USB flashdrives), and the like. For example, a memory 306 included in computing device 300 can store computer-readable and computer-executable instructions or software for implementing exemplary embodiments. Computing device 300 also includes a processor 302 and an associated core 304, and optionally, one or more additional processor(s) 302' and associated core(s) 304' (for example, in the case of computer systems having multiple processors/cores), for executing computer-readable and computer-executable instructions or software stored in memory 306 and other programs for controlling system hardware. Processor 302 and processor(s) 302' can each be a single core processor or multiple core (304 and 304') processor.

Computing device 300 may include a browser application 315 and a browser cache 317. As described above, browser application 315 can enable a user to select files and/or file links, and receive a file.

Virtualization can be employed in computing device 300 so that infrastructure and resources in the computing device can be shared dynamically. A virtual machine 314 can be provided to handle a process running on multiple processors so that the process appears to be using only one computing resource rather than multiple computing resources. Multiple virtual machines can also be used with one processor.

Memory 306 can include a computer system memory or random access memory, such as DRAM, SRAM, EDO RAM, and the like. Memory 306 can include other varieties of memory as well, or combinations thereof. In some embodiments, a user can interact with computing device 300 through a visual display device 318, such as a touch screen display or computer monitor, which can display one or more user interfaces 319 that can be provided in accordance with exemplary embodiments, for example, the exemplary user interfaces. Visual display device 318 may also display other aspects, elements and/or information or data associated with exemplary embodiments. Computing device 300 may include other I/O devices for receiving input from a user, for example, a keyboard or any suitable multi-point touch interface 308, a pointing device 310 (e.g., a pen, stylus, mouse, or trackpad). The keyboard 308 and pointing device 310 may be coupled to visual display device 318. Computing device 300 may include other suitable conventional I/O peripherals.

Computing device 300 can also include one or more storage devices 324, such as a hard-drive, CD-ROM, or other computer readable media, for storing data and computer-readable instructions and/or software, that implements embodiments of the specialized computer file system, as described herein, or portions thereof. Exemplary storage device 324 can also store one or more storage devices for storing any suitable information required to implement exemplary embodiments.

Computing device 300 can include a network interface 312 configured to interface via one or more network devices 322 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 312 can include a built-in network adapter, network interface card, PCMCIA network card, card bus network adapter, wireless network adapter, USB network adapter, modem or any other device suitable for interfacing computing device 300 to any variety of network capable of communication and performing the operations described herein. Moreover, computing device 300 can be any computer system, such as a workstation, desktop computer, server, laptop, handheld computer, tablet computer (e.g., the iPad® tablet computer), mobile computing or communication device (e.g., the iPhone® communication device), or other form of computing or telecommunications device that is capable of communication and that has sufficient processor power and memory capacity to perform the operations described herein.

Computing device 300 can run any operating system 316, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, any operating systems for mobile computing devices, or any other operating system capable of running on the computing device and performing the operations described herein. In exemplary embodiments, the operating system 316 can be run in native mode or emulated mode. In an exemplary embodiment, the operating system 316 can be run on one or more cloud machine instances.

Figure 4:
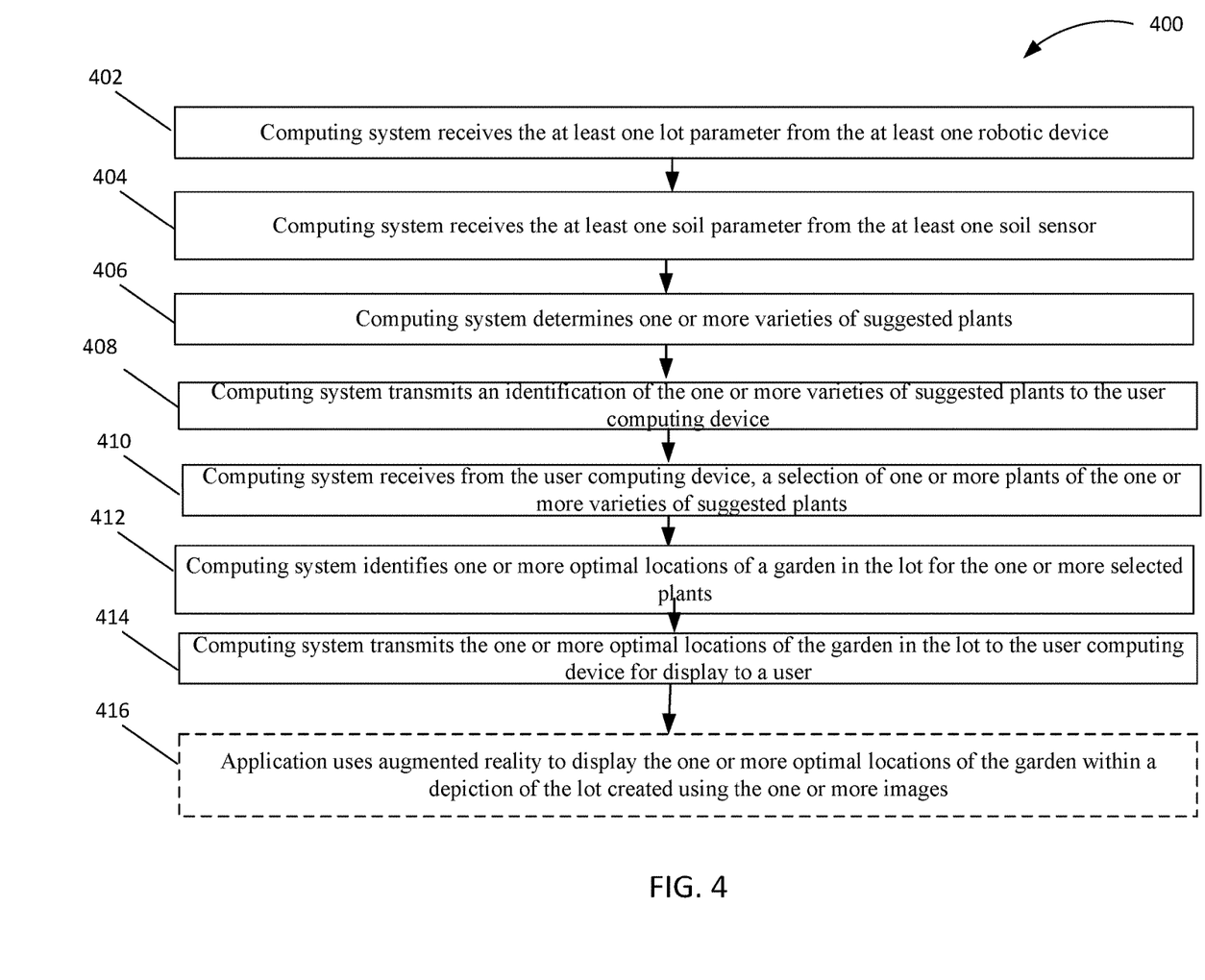
FIG. 4 is a flowchart illustrating an exemplary method for identifying and displaying one or more optimal locations of a garden in a lot to plant and grow suggested plant varieties, according to an example embodiment.

FIG. 4 is a flowchart illustrating an exemplary method 400 for identifying and displaying one or more optimal locations of a garden in a lot to plant and grow suggested plant varieties, in an embodiment. Method 400 is implemented using at least one robotic device positioned and configured to scan the lot and generate at least one lot parameter, at least one soil sensor positioned in soil in the lot and configured to generate at least one soil parameter, a storage device storing predefined criteria, and a computing system communicatively coupled to the at least one soil sensor, the at least one robotic device, the storage device, and a user computing device.

At step 402, the computing system receives the at least one lot parameter from the at least one robotic device. At step 404, the computing system receives the at least one soil parameter from the at least one soil sensor. In some embodiments, the robotic device is a rover, and the method is further implemented using the rover. The at least one sensor may be attached to the rover. At step 406, the computing system determines one or more varieties of suggested plants based on the at least one soil parameter and the at least one lot parameter. At step 408, the computing system transmits an identification of the one or more varieties of suggested plants to the user computing device which displays the identification of the one or more varieties of suggested plants. At step 410, the computing system receives from the user computing device, a selection of one or more plants of the one or more varieties of suggested plants.

At step 412, the computing system generates one or more optimal locations of a garden in the lot for the one or more selected plants based on the at least one lot parameter, the at least one soil parameter, and the predefined criteria. The one or more optimal locations of the garden in the lot includes at least one of an size, a shape, and an orientation of the garden in the lot. At step 414, the computing system transmits the one or more optimal locations of the garden in the lot to the user computing device for display to a user. In some embodiments, the method is further implemented via an application installed on the user computing device configured to capture one or more images of the lot. In such an embodiment, at step 416, augmented reality may be used to display the one or more optimal locations of the garden within a depiction of the lot created using the one or more images. In additional embodiments, the method further includes using augmented reality to display an arrangement of the one or more selected plants in the garden.

In one embodiment, the computing system may receive, from the user computing device, a new selection of one or more plants of the one or more varieties of suggested plants. The computing system may change the one or more optimal locations of the garden in the lot based on the new selection of the one or more plants of the one or more varieties of suggested plants and transmit the new optimal locations to the user computing device for display to a user.

The following description is presented to enable any person skilled in the art to create and use a computer system configuration and related method and systems for improving access to electronic data. Various modifications to the example embodiments will be readily apparent to those skilled in the art, and the generic principles defined herein may be applied to other embodiments and applications without departing from the spirit and scope of the invention. Moreover, in the following description, numerous details are set forth for the purpose of explanation. However, one of ordinary skill in the art will realize that the invention may be practiced without the use of these specific details. In other instances, well-known structures and processes are shown in block diagram form in order not to obscure the description of the invention with unnecessary detail. Thus, the present disclosure is not intended to be limited to the embodiments shown, but is to be accorded the widest scope consistent with the principles and features disclosed herein.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps can be replaced with a single element, component or step Likewise, a single element, component or step can be replaced with a plurality of elements, components or steps that serve the same purpose. Moreover, while exemplary embodiments have been shown and described with references to particular embodiments thereof, those of ordinary skill in the art will understand that various substitutions and alterations in form and detail can be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods can include more or fewer steps than those illustrated in the exemplary flowcharts, and that the steps in the exemplary flowcharts can be performed in a different order than the order shown in the illustrative flowcharts.

We claim:

1. A system for identifying and displaying one or more optimal locations within a lot for a garden, the system comprising:

at least one robotic device positioned and configured to scan a lot and to generate at least one lot parameter;

at least one soil sensor positionable in soil in the lot and configured to generate at least one soil parameter;

a storage device storing predefined criteria for associating plant varieties, lot parameters, and soil parameters with optimal lot locations; and a computing system communicatively coupled to the at least one soil sensor, the at least one robotic device, the storage device, and a user computing device, the computing system configured to execute a location optimization module that when executed:

receives the at least one lot parameter from the at least one robotic device;

receives the at least one soil parameter from the at least one soil sensor;

determines one or more varieties of suggested plants based on the at least one soil parameter and the at least one lot parameter;

transmits an identification of the one or more varieties of suggested plants to the user computing device, wherein the user computing device displays the identification of the one or more varieties of suggested plants;

receives, from the user computing device, a selection of one or more plants of the one or more varieties of suggested plants;

identifies one or more optimal locations for a garden within the lot for the selected one or more plants based on the at least one lot parameter, the at least one soil parameter and the predefined criteria, the one or more optimal locations representing a portion of the lot that is less than the entire lot; and
transmits the one or more optimal locations for the garden to the user computing device, wherein the user computing device displays the one or more optimal locations for the garden within the lot.

2. The system of claim 1, the system further comprising an application installed on the user computing device that when executed captures one or more images of the lot, the application configured to use augmented reality to display the one or more optimal locations for the garden within a depiction of the lot created using the one or more images.

3. The system of claim 2, wherein the application when executed generates an augmented reality display of an arrangement of the one or more varieties of suggested plants in the garden.

4. The system of claim 1 wherein the at least one robotic device is an autonomous rover and the at least one soil sensor is attached to the rover.

5. The system of claim 1 wherein the at least one robotic device is an autonomous unmanned aerial vehicle.

6. The system of claim 1, wherein the at least one lot parameter includes at least one of a lot area size, a geographic location, a date, an identification of water sources, an elevation, an identification of buildings located in the lot, a current garden layout, an identification of trees and shrubbery, and shade density information for locations within the lot.

7. The system of claim 1, wherein the at least one soil parameter includes at least one of a moisture content level of the soil, a potential hydrogen (pH) level of the soil, a temperature level of the soil, and an intensity level of light that reaches the soil.

8. The system of claim 1, wherein the location optimization module when executed receives dimensions of the lot from the user computing device, and determines the one or more optimal locations of the garden within the dimensions of the lot.

9. The system of claim 1, wherein the location optimization module when executed:
receives, from the user computing device, a new selection of one or more plants of the one or more varieties of suggested plants; and
changes at least one optimal location for the garden within the lot based on the new selection of one or more plants of the one or more varieties of suggested plants.

10. The system of claim 1, wherein the one or more optimal locations for the garden within the lot includes at least one of an size, a shape, and an orientation of the garden within the lot.

11. A system for identifying and displaying one or more optimal locations within a lot for a garden, the system comprising:
at least one robotic device positioned and configured to scan a lot and to generate at least one lot parameter;
a storage device storing predefined criteria for associating plant varieties and lot parameters with optimal lot locations;
a computing system communicatively coupled to the at least one soil sensor, the at least one robotic device, the storage device, and a user computing device, the computing system configured to execute a location optimization module; and
an application installed on the user computing device and configured to capture one or more images of the lot, wherein the location optimization module when executed:
receives the at least one lot parameter from the at least one robotic device,
determines one or more varieties of suggested plants based on the at least one lot parameter,
transmits an identification of the one or more varieties of suggested plants to the user computing device, wherein the user computing device displays the identification of the one or more varieties of suggested plants,
receives, from the user computing device, a selection of one or more plants of the one or more varieties of suggested plants,
identifies one or more optimal locations for a garden within the lot for the one or more selected plants based on the at least one lot parameter and the predefined criteria, the one or more optimal locations representing a portion of the lot that is less than the entire lot, and
transmits the one or more optimal locations for the garden to the user computing device, and
wherein the application is configured to use augmented reality to display the one or more optimal locations for the garden within a depiction of the lot created using the one or more images.

12. A computer-implemented method for generating and displaying one or more optimal locations within a lot for a garden within a lot, the method comprising:
receiving, with a computing system, at least one lot parameter generated by at least one robotic device scanning the lot;
receiving, with the computing system, from a sensor positioned in soil in the lot at least one soil parameter;
determining, with the computing system, one or more varieties of suggested plants based on the at least one soil parameter and the at least one lot parameter;
transmitting, from the computing system, an identification of the one or more varieties of suggested plants to a user computing device, wherein the user computing device displays the identification of the one or more varieties of suggested plants;
receiving, with the computing system, from the user computing device, a selection of one or more plants of the one or more varieties of suggested plants;
identifying, with the computing system, one or more optimal locations for a garden within the lot for the selected one or more plants based on the at least one lot parameter and previously stored predefined criteria for associating plant varieties, lot parameters, and soil parameters with optimal locations, the one or more optimal locations representing a portion of the lot that is less than the entire lot; and
transmitting, by the computing system, the one or more optimal locations for the garden within the lot to the user computing device, wherein the user computing device displays the one or more optimal locations for the garden within the lot.

13. The method of claim 12 wherein the at least one robotic device is an autonomous rover and the at least one soil sensor is attached to the rover.

14. The method of claim 12, wherein the at least one lot parameter includes at least one of a lot area size, a geographic location, a date, an identification of water sources, an elevation, an identification of buildings located in the lot, a current garden layout, an identification of trees and shrubbery, and shade density information of locations in the lot.

15. The method of claim 12, wherein the at least one soil parameter includes at least one of a moisture content level of the soil, a potential hydrogen (pH) level of the soil, a temperature level of the soil, and an intensity level of light that reaches the soil.

16. The method of claim 12, the method further implemented via an application installed on the user computing device configured to capture one or more images of the lot, the method further comprising using, via the application, augmented reality to display the one or more optimal locations of the garden within a depiction of the lot created using the one or more images.

17. The method of claim 16, the method further comprising using, by the application, augmented reality to display an arrangement of the one or more varieties of suggested plants in the garden.

18. The method of claim 12, the method further comprising receiving, by the computing system, dimensions of the lot from the user computing device, and determining, by the computing system, the one or more optimal locations of the garden within the dimensions of the lot.

19. The method of claim 12, further comprising:
 receiving, by the computing system, from the user computing device, a new selection of one or more plants of the one or more varieties of suggested plants; and
 changing, by the computing system, the one or more optimal locations for the garden within the lot based on the new selection of the one or more plants of the one or more varieties of suggested plants.

20. The method of claim 12, wherein the one or more optimal locations for the garden within the lot includes at least one of an size, a shape, and an orientation for the garden within the lot.

* * * * *